(12) United States Patent
Gallenkamp et al.

(10) Patent No.: US 10,710,972 B2
(45) Date of Patent: Jul. 14, 2020

(54) METHOD FOR PREPARING SUBSTITUTED 2,3-DIHYDRO-1-BENZOFURAN DERIVATIVES

(71) Applicant: BAYER CROPSCIENCE AKTIENGESELLSCHAFT, Monheim am Rhein (DE)

(72) Inventors: Daniel Gallenkamp, Wuppertal (DE); Mark James Ford, Wiesbaden-Breckenheim (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 1 day.

(21) Appl. No.: 16/324,390

(22) PCT Filed: Aug. 7, 2017

(86) PCT No.: PCT/EP2017/069933
§ 371 (c)(1),
(2) Date: Feb. 8, 2019

(87) PCT Pub. No.: WO2018/029141
PCT Pub. Date: Feb. 15, 2018

(65) Prior Publication Data
US 2020/0190047 A1 Jun. 18, 2020

(30) Foreign Application Priority Data
Aug. 12, 2016 (EP) .................... 16183949

(51) Int. Cl.
*C07D 307/79* (2006.01)
*C07C 245/20* (2006.01)
(52) U.S. Cl.
CPC .......... *C07D 307/79* (2013.01); *C07C 245/20* (2013.01)
(58) Field of Classification Search
CPC ............ C07D 307/79; C07C 245/20
See application file for complete search history.

(56) References Cited

U.S. PATENT DOCUMENTS

| | | | |
|---|---|---|---|
| 8,759,527 | B2 | 6/2014 | Tsuchiya et al. |
| 9,006,266 | B2 | 4/2015 | Tsuchiya et al. |
| 9,150,565 | B2 | 10/2015 | Tsuchiya et al. |
| 9,434,723 | B2 | 9/2016 | Tsuchiya et al. |
| 9,770,027 | B2 | 9/2017 | Tsuchiya et al. |
| 9,930,890 | B2 | 4/2018 | Tsuchiya et al. |
| 2006/0166985 | A1 | 7/2006 | Borthwick et al. |
| 2010/0311735 | A1 | 12/2010 | Tsantrizos et al. |
| 2013/0197231 | A1 | 8/2013 | Tsantrizos et al. |
| 2014/0296228 | A1 | 10/2014 | Tsantrizos et al. |
| 2015/0329566 | A1 | 11/2015 | Oosting et al. |
| 2018/0007903 | A1 | 1/2018 | Tsuchiya et al. |

FOREIGN PATENT DOCUMENTS

| | | |
|---|---|---|
| WO | 2004/052851 A1 | 6/2004 |
| WO | 2009/062285 A1 | 5/2009 |
| WO | 2012/025557 A1 | 3/2012 |
| WO | 2014/091167 A2 | 6/2014 |

OTHER PUBLICATIONS

Zhu, Jingyang et al., "Copper (I)—catalyzed intramolecular cyclization reaction of 2-(2'chlorophenyl)ethanol to give 2,3-dihydrobenzofuran", Tetrahedron Letters, May 1, 2000, pp. 4011-4014, vol. 41, No. 21.
Bakke, Jan M. et al., "Synthesis of 2,3-Dihydrobenzofuran", Acta Chemica Scandinavica, Series B: Organic Chemistry and Biochemistry, 1980, p. 73, vol. 34b, No. 1.
Bennet, G.M. et al., "52. A synthesis of dihydroindole, dihydrothionaphthen, and dihydrobenzofuran", Journal of the Chemical Society, 1941, pp. 287-288.
Gao, Hongyin et al., "Transition-Metal-Free Direct Arylation: Synthesis of Halogenated 2-Amino-2'-hydroxy-1,1'-biaryls and Mechanism by DFT Calculation", Journal of the American Chemical Society, Mar. 4, 2013, pp. 7086-7089, vol. 135.
Kumar, Amit et al., "Double functionalization of 2-amino-2'-hydroxy-1,1'-biaryls: synthesis of 4-nitro-dibenzofurans and benzofuroindoles", Royal Society of Chemistry, 2015, pp. 44728-44741, vol. 5.
International Search Report of International Patent Application No. PCT/EP2017/069933 dated Nov. 16, 2017.

*Primary Examiner* — Joseph R Kosack
(74) *Attorney, Agent, or Firm* — McBee Moore & Vanik IP, LLC

(57) ABSTRACT

The present invention relates to a method for preparing substituted 2,3-dihydro-1-benzofuran derivatives.

9 Claims, No Drawings

METHOD FOR PREPARING SUBSTITUTED 2,3-DIHYDRO-1-BENZOFURAN DERIVATIVES

CROSS-REFERENCE TO RELATED APPLICATIONS

This application is a National Stage entry of International Application No. PCT/EP2017/069933, filed 7 Aug. 2017, which claims priority to European Patent Application No. 16183949.3, filed 12 Aug. 2016.

BACKGROUND

Description of Related Art

The present invention relates to a method for preparing substituted 2,3-dihydro-1-benzofuran derivatives.

Substituted 2,3-dihydrobenzofuran derivatives are useful intermediates in the preparation of substituted styrene derivatives, which are in turn useful intermediates in the preparation of active agrochemical ingredients (see WO 2012/025557 for example).

A possible method for preparing 4-chloro-2,3-dihydro-1-benzofuran is described in the literature. The preparation is effected by intramolecular cyclization of 2-(2,6-dichlorophenyl)ethanol using 1.2 equivalents of NaH in the presence of catalytic amounts of CuCl (*Tetrahedron Lett.* 2000, 41, 4011) in toluene at 100° C. Disadvantages of this method are that 2-(2,6-dichlorophenyl)ethanol as raw material is not available on an industrial scale and has to be prepared by a multi-stage cost-intensive reaction sequence, NaH is unsuitable as base on an industrial scale and Cu-heavy metal waste is produced.

A method for preparing 4-methyl-2,3-dihydro-1-benzofuran is known from WO 2009/062285. The preparation is effected by cyclization of 2-bromo-1-(2-hydroxy-6-methylphenyl)ethanone to give 4-methylbenzofuran-3-one and subsequent reduction to give 4-methyl-2,3-dihydro-1-benzofuran. Disadvantages are that the starting material for this method also has to be prepared by a complex multi-stage reaction sequence and the yield over two stages is only 42%.

An alternative and general possibility for preparing 2,3-dihydrobenzofurans consists of cyclizing the diazonium salt compounds of 2-(2-aminophenyl)ethanol derivatives. For example, the treatment of 2-(2-aminophenyl)ethanol with $NaNO_2$ and $H_2SO4$ in aqueous solution at 0° C. and subsequent heating of the reaction mixture to 50° C. affords 2,3-dihydrobenzofuran in a yield of 50% (*J. Chem. Soc.* 1941, 287). The reaction is described under identical conditions in *Acta Chem. Scand. B* 1980, B34, 73 with a yield of 35% of 2,3-dihydrobenzofuran and 50% of 2-(2-hydroxyethyl)phenol as secondary component. WO 2004/052851 describes the reaction of 2-(2-amino-5-chlorophenyl)propane-1,3-diol to give (5-chloro-2,3-dihydro-1-benzofuran-3-yl)methanol under the reaction conditions described above without a yield being reported. A disadvantage of this method is that in the reaction of 2-(2-amino-6-chlorophenyl)ethanol under these reaction conditions, in addition to 4-chloro-2,3-dihydro-1-benzofuran, 3-chloro-2-(2-hydroxyethyl)phenol is formed as secondary component. The yield of 4-chloro-2,3-dihydro-1-benzofuran is thereby reduced and an additional purification step is required. *J. Am. Chem. Soc.* 2013, 135, 7086 describes the reaction of 2'-amino-3'-bromobiphenyl-2-ol with 1.2 equivalents of $NaNO_2$ in a mixture of TFA/water 20:1 at 0° C. and subsequent heating of the reaction mixture to 70° C., whereupon 4-bromodibenzo[b,d]furan may be isolated in a yield of 75%. Similar reaction conditions are described in *RSC Adv.* 2015, 5, 44728 for the cyclization (and simultaneous nitration) of, for example, 2'-amino-5-chloro-4'-methylbiphenyl-2-ol to give 2-chloro-7-methyl-4-nitrodibenzo[b,d]furan. A disadvantage of this method is that in the reaction of 2-(2-amino-6-chlorophenyl)ethanol under these reaction conditions, in addition to 4-chloro-2,3-dihydro-1-benzofuran, 3-chloro-2-(2-hydroxyethyl)phenyl trifluoroacetate is formed as secondary component. The yield of 4-chloro-2,3-dihydro-1-benzofuran is thereby reduced and an additional purification step is required.

SUMMARY

Due to the importance of substituted 2,3-dihydrobenzofuran derivatives as a unit for synthesis of novel active agrochemical ingredients, the problem addressed is that of finding a method which can be used on an industrial scale and inexpensively and which circumvents the disadvantages described above. It is also desirable to obtain the specific 2,3-dihydro-1-benzofuran derivatives with high yield and high purity, such that the target compound preferably does not have to be subjected to any further potentially complex purification.

This object was achieved by a method for preparing substituted 2,3-dihydro-1-benzofuran derivatives of the formula (I):

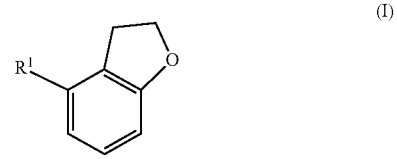

in which
R$^1$ is Cl (Ia), Br (Ib) or methyl (Ic),
characterized in that an aniline of the formula (II)

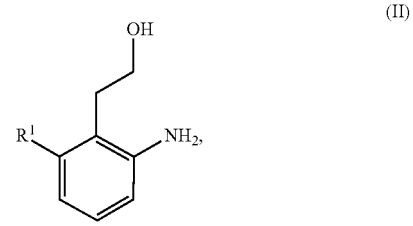

in which
R$^1$ is Cl, Br or methyl, is reacted in the presence of organic nitrite and organic or inorganic acids in organic solvents to give the diazonium salt of the formula (III),

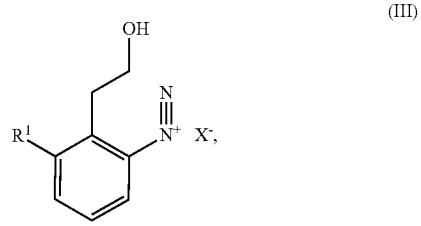

in which
R¹ is Cl, Br or methyl,
X⁻ is the counterion of the organic or inorganic acid,
which further reacts by heating to give compounds of the formula (I).

DETAILED DESCRIPTION OF A PREFERRED EMBODIMENT

Preference is given to a method according to the invention in which the radical definitions of the formulae (I), (II), and (III) are as follows:
R¹ is Cl,
X⁻ is Cl⁻, HSO₄⁻, Cl₃COO⁻, F₃CCOO⁻.

A further aspect of the present invention are salts of the compound of the formula (IIIa):

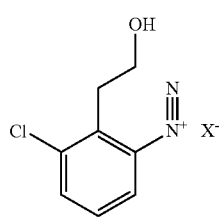

(IIIa)

in which
X is Cl⁻, HSO₄⁻, Cl₃COO⁻, F₃CCOO⁻.

DESCRIPTION OF THE PROCESS

The reaction according to the invention is shown in Scheme 1.

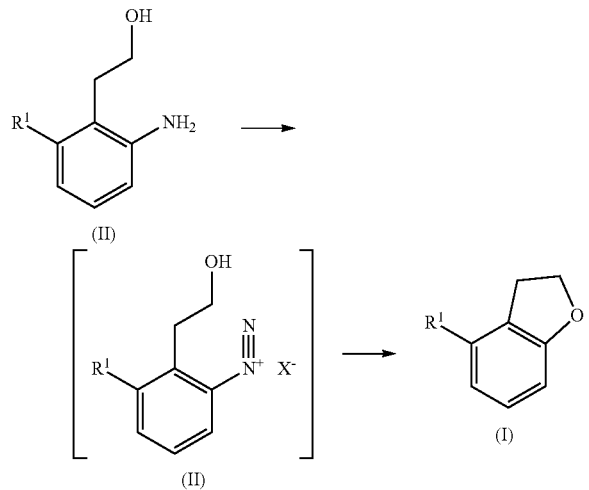

Scheme 1

The desired 2,3-dihydro-1-benzofuran derivatives of the general formula (I) are obtained in good yields and in high purity with the method according to the invention—reaction of the aniline of the formula (II) to give diazonium salt compounds of the formula (III) in the presence of organic nitrite and inorganic or organic acids in an organic solvent and subsequent further reaction to give compounds of the formula (I) by heating.

Surprisingly, higher yields and purities are achieved by using organic nitrites, preferably alkyl nitrites, in organic solvents and the formation of secondary components is suppressed.

Useful solvents for the process according to the invention in principle include any organic aprotic solvents or solvent mixtures that are inert under the reaction conditions, including: nitriles such as acetonitrile, propionitrile and butyronitrile; hydrocarbons and halogenated hydrocarbons such as hexane, heptane, cyclohexane, methylcyclohexane, toluene, ortho-xylene, meta-xylene, para-xylene, mesitylene, chlorbenzene, ortho-dichlorobenzene, dichloromethane, 1,2-dichloroethane, 1-chlorobutane, anisole or nitrobenzene. Preferably, the solvent is selected from the group of the hydrocarbons and halogenated hydrocarbons: hexane, heptane, cyclohexane, methylcyclohexane, toluene, ortho-xylene, meta-xylene, para-xylene, mesitylene, chlorobenzene, ortho-dichlorobenzene, dichloromethane, 1,2-dichloroethane, 1-chlorobutane, anisole, nitrobenzene or mixtures of these solvents, or the nitriles: acetonitrile, propionitrile, butyronitrile. Particular preference is given to using 1,2-dichloroethane, 1-chlorobutane, dichloromethane, toluene, xylene, chlorobenzene, 1,2-dichlorobenzene and/or acetonitrile.

Suitable inorganic acids are hydrochloric acid and sulphuric acid.

Suitable organic acids are trifluoroacetic acid (TFA) and trichloroacetic acid (TCA).

Suitable organic nitrites are alkyl nitrites. Preference is given to using $C_1$-$C_6$-alkyl nitrites (such as isopropyl nitrite, n-butyl nitrite, isobutyl nitrite, tert-butyl nitrite, pentyl nitrite or isopentyl nitrite). Particular preference is given to using organic nitrites selected from isopropyl nitrite, n-butyl nitrite, isobutyl nitrite, tert-butyl nitrite, pentyl nitrite and isopentyl nitrite. Very particular preference is given to using n-butyl nitrite, tert-butyl nitrite and/or isopentyl nitrite.

Particularly preferred are the following combinations of the above-described groups of solvents, organic nitrites and acids:

a) one or more nitriles as solvent, one or more $C_1$-$C_6$-alkyl nitrites as organic nitrite and sulphuric acid or hydrochloric acid as acid;

b) hydrocarbons and/or halogenated hydrocarbons as solvent, one or more $C_1$-$C_6$-alkyl nitrites as organic nitrite and trifluoroacetic acid or trichloroacetic acid as acid.

Very particularly preferred are the following combinations of the above-described groups of solvents, organic nitrites and acids:

a) 1,2-dichloroethane, 1-chlorobutane, dichloromethane, chlorobenzene, toluene, xylene and/or 1,2-dichlorobenzene as solvent in combination with trifluoroacetic acid or trichloroacetic acid as acid in combination with n-butyl nitrite, tert-butyl nitrite and/or isopentyl nitrite as nitrite;

b) acetonitrile, propionitrile and/or butyronitrile as solvent in combination with sulphuric acid or hydrochloric acid as acid in combination with n-butyl nitrite, tert-butyl nitrite and/or isopentyl nitrite as nitrite.

The temperature in the method according to the invention can be varied within wide limits. Typically, the diazonium salt compounds of the formula (III) are formed at a temperature of 0° C. to 20° C., preferably 0° C. to 10° C. Particular preference is given to conducting the reaction at a temperature in the range of 0° C. to 5° C. For the further reaction of the compounds of the formula (III) to give compounds of the formula (I), temperatures of 20° C. to 80° C., preferably 60 to 80° C., are typically employed.

The method according to the invention is typically conducted at standard pressure. It is also possible to conduct the reaction under reduced pressure or at elevated pressure (positive pressure).

The molar ratios of the compound of the formula (II) to acids of the group described above may be varied within wide limits. Typically, molar ratios from 1:1 to 1:3, preferably from 1:2 to 1:3, are employed. Particular preference is given to a molar ratio of 1:2.

The molar ratios of the compound of the formula (II) to nitrites of the group described above may be varied within wide limits. Typically, molar ratios from 1:1 to 1:2, preferably from 1:1 to 1:1.5, are employed. Particular preference is given to a molar ratio of 1:1.1.

The anilines of the formula (II) are known from the literature and some are available in industrial amounts (see, for example, *Tetrahedron Lett.* 2000, 41, 6319; *Tetrahedron Lett.* 1993, 34, 1057; *J. Org. Chem.* 1990, 55, 580).

The reaction time of the reaction for the formation of the diazonium salt compounds of the formula (III) is short and is in the range of 0.5 to 2 hours. A longer reaction time is possible, but is not economically worthwhile. The reaction time of the further reaction of the compounds of the formula (III) to give compounds of the formula (I) is short and is in the range of 0.5 to 2 hours. A longer reaction time is possible, but is not economically worthwhile.

EXAMPLES

The present invention is elucidated in more detail by the examples which follow, without restricting the invention to these examples.

4-Chloro-2,3-dihydro-1-benzofuran (Ia)

Trifluoroacetic acid (15.4 ml, 200.4 mmol) was added to a solution of 2-(2-amino-6-chlorophenyl)ethanol (IIa) (17.2 g, 100.2 mmol) in 1,2-dichloroethane (55 ml) at 0-5° C. n-Butyl nitrite (95%, 13.6 ml, 110.2 mmol) was metered in over a period of 1 h at a temperature of 0-5° C. and, after addition was complete, the mixture was stirred at this temperature for 1 h. The resulting diazonium salt was not isolated and was directly reacted further. Analytical data for the diazonium trifluoroacetate salt (IIIa, X=F$_3$CCOO$^-$) are as follows: $^1$H-NMR (DMSO-d6, 400 MHz) δ (ppm)=8.71 (dd, J=8.3, 1.2 Hz, 1H), 8.41 (dd, J=8.3, 1.1 Hz, 1 H), 7.90 (t, J=8.3 Hz, 1 H), 3.75 (t, J=5.6 Hz, 2 H), 3.33 (t, J=5.6 Hz, 2 H); $^1$H-NMR (CDCl$_3$, 400 MHz) δ (ppm)=8.70 (dd, J=8.3, 1.0 Hz, 1 H), 8.08 (dd, J=8.3, 1.1 Hz, 1 H), 7.63 (t, J=8.3 Hz, 1 H), 3.93 (t, J=5.3 Hz, 2 H), 3.37 (t, J=5.3 Hz, 2 H). Analytical data for the diazonium trichloroacetate salt (IIIa, X=Cl$_3$CCOO$^-$) are as follows: $^1$H-NMR (DMSO-d6, 400 MHz) δ (ppm) =7.83 (dd, J=8.0, 1.1 Hz, 1 H), 7.62 (dd, J=8.0, 1.1 Hz, 1 H), 7.48 (t, J=8.0 Hz, 1 H), 3.57 (t, J=7.1 Hz, 2 H), 3.39 (t, J=7.1 Hz, 2 H). Analytical data for the diazonium chloride salt (IIIa, X=Cl$^-$) are as follows: $^1$H-NMR (DMSO-d6, 400 MHz) δ (ppm)=8.81 (dd, J=8.4, 1.1 Hz, 1 H), 8.41 (dd, J=8.2, 1.0 Hz, 1 H), 7.91 (t, J=8.3 Hz, 1 H), 3.73 (t, J=5.6 Hz, 2 H), 3.33 (t, J=5.6 Hz, 2 H). Analytical data for the diazonium hydrogen sulphate salt (IIIa, X=HSO$_4^-$) are as follows: $^1$H-NMR (DMSO-d6, 400 MHz) δ (ppm)=8.73 (dd, J=8.3, 1.1 Hz, 1 H), 8.40 (dd, J=8.3, 1.1 Hz, 1 H), 7.90 (t, J=8.3 Hz, 1 H), 3.74 (t, J=5.6 Hz, 2 H), 3.33 (t, J=5.6 Hz, 2 H).

The above solution was metered into 1,2-dichloroethane (30 ml) over a period of 1 h at 70-80° C. and, after addition was complete, the mixture was stirred at this temperature for a further 30 min The reaction solution was cooled to 20° C. and washed with 10% HCl solution (20 ml). The organic phase was dried over magnesium sulphate, filtered and concentrated under reduced pressure. The residue was then fractionally distilled under reduced pressure (b.p. 89-91° C./10 mbar, 11.9 g, 77% of theory). $^1$H-NMR (CDCl$_3$, 400 MHz) δ (ppm) =7.04 (tt, J=8.0, 0.7 Hz, 1 H), 6.82 (dd, J=8.0, 0.7 Hz, 1 H), 6.67 (d, J=8.1 Hz, 1 H), 4.60 (t, J=8.7 Hz, 2 H), 3.25 (t, J=8.7 Hz, 2 H).

4-Bromo-2,3-dihydro-1-benzofuran (Ib)

b.p. 106 -108° C./10 mbar; $^1$H-NMR (DMSO-d6, 400 MHz) δ (ppm)=7.05 (t, J=7.7 Hz, 1 H), 7.01 (dd, J=8.1, 1.1 Hz, 1 H), 6.76 (dd, J=7.6, 1.1 Hz, 1 H), 4.58 (t, J=8.7 Hz, 2 H), 3.17 (t, J=8.7 Hz, 2 H).

4-Methyl-2,3-dihydro-1-benzofuran (Ic)

b.p. 89-91° C./10 mbar; $^1$H-NMR (DMSO-d6, 400 MHz) δ (ppm)=6.96 (t, J=7.7 Hz, 1 H), 6.63 (d, J=7.6 Hz, 1 H), 6.55 (d, J=8.0 Hz, 1 H), 4.50 (t, J=8.7 Hz, 2 H), 3.08 (t, J=8.7 Hz, 2 H), 2.19 (s, 3 H).

COMPARATIVE EXAMPLE

Preparation of 4-chloro-2,3-dihydro-1-benzofuran (Ia) obtaining 3-chloro-2-(2-hydroxyethyl)phenol as Secondary Component

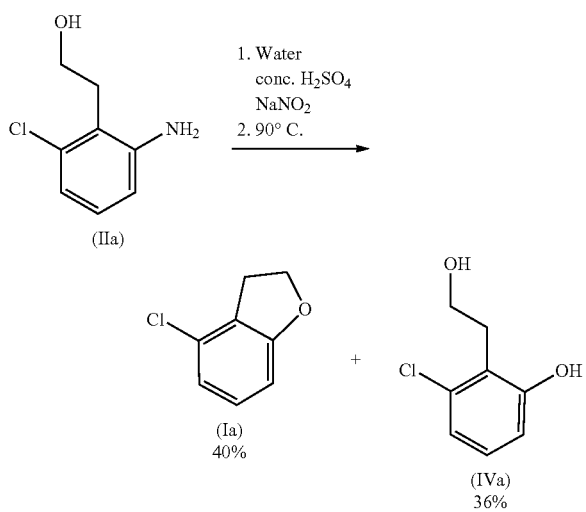

2-(2-Amino-6-chlorophenyl)ethanol (IIa) (10.0 g, 58.3 mmol) was taken up in a mixture of water (250 ml) and concentrated sulphuric acid (25.0 ml) and cooled to 0° C. A solution of sodium nitrite (7.24 g, 104.9 mmol) in water (50.0 ml) was metered in over a period of 1 h at a temperature of 0-5° C. and, after addition was complete, the mixture was stirred further at 0° C. for 1 h. HPLC showed complete conversion to the diazonium salt. The resulting diazonium salt was not isolated and was directly reacted further.

The above solution was metered into water (50 ml) over a period of 1 h at 80-90° C. and, after addition was complete, the mixture was stirred at this temperature for a further 30 min. HPLC shows complete conversion of the diazonium salt to 4-chloro-2,3-dihydro-1-benzofuran (Ia, 41 area % HPLC)) and 3-chloro-2-(2-hydroxyethyl)phenol (IVa, 56 area % HPLC). The reaction mixture was cooled to 20° C. and extracted three times with ethyl acetate (100 ml each time). The combined organic phases were washed three times with 5% NaOH (100 ml each time). The remaining organic phase was washed with saturated sodium chloride solution, dried over MgSO$_4$ and concentrated on a rotary evaporator. This gave 4-chloro-2,3-dihydro-1-benzofuran (Ia) as an orange-yellowish oil (4.0 g, purity: 91 area % HPLC, yield: 40% of theory, analytical data: see inventive example). The combined aqueous NaOH phases were brought to a pH of 1-2 by addition of 20% HCl and then extracted three times with EtOAc (100 ml each time). The combined organic phases were washed with saturated sodium chloride solution, dried over $MgSO_4$ and concentrated on the rotary evaporator. This gave 3-chloro-2-(2-hydroxyethyl)phenol (IVa) as an orange-yellowish oil (4.0 g, purity: 96 area % HPLC, yield: 38% of theory) with the following analytical data: $^1$H-NMR ($CDCl_3$, 400 MHz) δ (ppm)=7.07 (t, J=8.1 Hz, 1 H), 6.97 (d, J=8.1 Hz, 1 H), 6.85 (d, J=8.1 Hz, 1 H), 4.01 (t, J=8.5 Hz, 2 H), 3.12 (t, J=8.5 Hz, 2 H).

The invention claimed is:

1. Method for preparing substituted 2,3-dihydro-1-benzofuran derivative of formula (I):

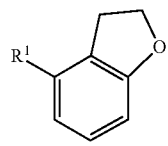
(I)

in which
R$^1$ is Cl (Ia), Br (Ib) or methyl (Ic),
comprising reacting an aniline of the formula (II)

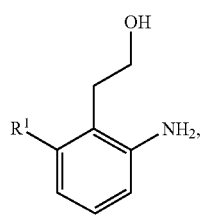
(II)

in which
R$^1$ is Cl, Br or methyl in the presence of one or more organic nitrite and organic or inorganic acids in one or more organic solvents to give a diazonium salt of formula (III),

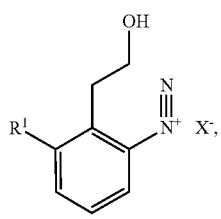
(III)

in which
R$^1$ is Cl, Br or methyl,
X$^-$ is a counterion of a organic or inorganic acid, which further reacts by heating to give one or more compounds of formula (I).

2. Method according to claim 1, wherein R$^1$ is Cl.

3. Method according to claim 1, wherein X$^-$ is Cl$^-$, $HSO_4^-$, $Cl_3COO^-$ or $F_3CCOO^-$.

4. Method according to claim 1, wherein one or more nitriles, hydrocarbons and/or halogenated hydrocarbons are used as solvent.

5. Method according to claim 1, wherein solvent used comprises dichloromethane, 1,2-dichloroethane, 1-chlorobutane, toluene, xylene, chlorobenzene, 1,2-dichlorobenzene and/or acetonitrile.

6. Method according to claim 1, wherein an organic nitrite used comprises a $C_1$-$C_6$-alkyl nitrite.

7. Method according to claim 1, wherein one of the following combinations of solvent, organic nitrite and acid is used for the reaction:

a) one or more nitriles as solvent, one or more $C_1$-$C_6$-alkyl nitrites as organic nitrite and sulphuric acid or hydrochloric acid as acid;

b) hydrocarbons and/or halogenated hydrocarbons as solvent, one or more $C_1$-$C_6$-alkyl nitrites as organic nitrite and trifluoroacetic acid or trichloroacetic acid as acids.

8. Method according to claim 1, wherein one of the following combinations of solvent, organic nitrite and acid is used for the reaction:

a) acetonitrile, propionitrile and/or butyronitrile in combination with sulphuric acid or hydrochloric acid in combination with n-butyl nitrite, tert-butyl nitrite and/or isopentyl nitrite;

b) 1,2-dichloroethane, dichloromethane, 1-chlorobutane, toluene, xylene, chlorobenzene and/or 1,2-dichlorobenzene in combination with trifluoroacetic acid or trichloroacetic acid in combination with n-butyl nitrite, tert-butyl nitrite and/or isopentyl nitrite.

9. Compound of formula (IIIa):

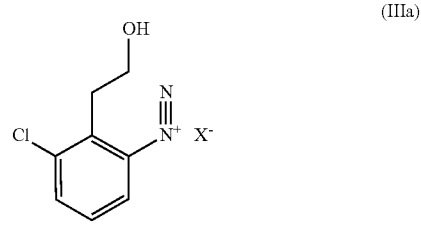
(IIIa)

in which
X$^-$ is Cl$^-$, $HSO_4^-$, $Cl_3COO^-$ or $F_3CCOO^-$.

* * * * *